United States Patent
Carim

[11] Patent Number: 5,813,981
[45] Date of Patent: Sep. 29, 1998

[54] TAB STYLE ELECTRODE

[75] Inventor: Hatim M. Carim, West St. Paul, Minn.

[73] Assignee: Minnesota Mining and Manufacturing Company, St. Paul, Minn.

[21] Appl. No.: 581,432

[22] Filed: Dec. 29, 1995

[51] Int. Cl.⁶ ............................................. A61B 5/0408
[52] U.S. Cl. ........................................ 600/372; 128/639
[58] Field of Search ...................... 607/152; 128/639–644

[56] References Cited

U.S. PATENT DOCUMENTS

| | | | |
|---|---|---|---|
| 4,166,453 | 9/1979 | McClelland | 128/639 |
| 4,350,165 | 9/1982 | Striese | 128/640 |
| 4,409,981 | 10/1983 | Lundberg | 128/640 |
| 4,522,211 | 6/1985 | Bare et al. | 128/640 |
| 4,524,087 | 6/1985 | Engel | 427/2 |
| 4,539,996 | 9/1985 | Engel | 128/640 |
| 4,657,023 | 4/1987 | Kuhn | 128/640 |
| 4,715,382 | 12/1987 | Strand | 128/640 |
| 4,795,516 | 1/1989 | Strand | 156/235 |
| 4,798,642 | 1/1989 | Craighead et al. | 156/252 |
| 4,838,273 | 6/1989 | Cartmell | 128/640 |
| 4,846,185 | 7/1989 | Carim | 128/641 |
| 4,848,353 | 7/1989 | Engel | 128/640 |
| 5,012,810 | 5/1991 | Strand et al. | 128/640 |
| 5,215,087 | 6/1993 | Anderson et al. | 128/640 |
| 5,225,473 | 7/1993 | Duan | 524/388 |
| 5,230,701 | 7/1993 | Meyer et al. | 602/76 |
| 5,261,402 | 11/1993 | DiSabito | 128/640 |
| 5,276,079 | 1/1994 | Duan et al. | 524/386 |
| 5,338,490 | 8/1994 | Dietz et al. | 252/500 |
| 5,362,420 | 11/1994 | Itoh et al. | 252/500 |
| 5,385,679 | 1/1995 | Uy et al. | 252/500 |
| 5,520,180 | 5/1996 | Uy et al. | 607/152 |

FOREIGN PATENT DOCUMENTS

| | | | |
|---|---|---|---|
| 1269417 | 5/1990 | Canada | 326/17.4 |
| 0210020 | 7/1986 | European Pat. Off. | A61B 5/04 |
| WO 94/12585 | 6/1994 | WIPO | C09J 171/00 |
| WO 94/26950 | 11/1994 | WIPO | C23C 14/20 |
| WO 95/20350 | 8/1995 | WIPO | A61B 5/0408 |
| WO 95/20634 | 8/1995 | WIPO | C09J 7/02 |

*Primary Examiner*—John P. Lacyk
*Assistant Examiner*—David M. Ruddy
*Attorney, Agent, or Firm*—Gary L. Griswold; Walter N. Kirn; John H. Hornickel

[57] ABSTRACT

The present invention discloses a biomedical electrode of low profile, multi-layer construction wherein an electrically conductive tab contacts ionically conductive medium through an aperture of an insulative backing.

8 Claims, 1 Drawing Sheet

TAB STYLE ELECTRODE

FIELD OF THE INVENTION

This invention relates to biomedical electrodes having a low profile and a multi-layer construction.

BACKGROUND OF THE INVENTION

Biomedical electrodes are used in the fields of electrocardiography and for transcutaneous electrical nerve stimulation. A number of biomedical electrode constructions have employed an insulative outer layer through which an electrically conductive tab extends to provide a low profile, multi-layer construction. Representative examples of such constructions are disclosed in the embodiments shown in U.S. Pat. No. 5,012,810 (Strand et al.).

Another low profile multi-layer construction employs an electrically conductive tab which remains below the surface of the outermost layer but is accessible to the outside through an aperture in the outermost layer. A representative example of this electrode construction is disclosed in U.S. Pat. No. 5,215,087 (Anderson et al.).

Other biomedical electrode constructions involve an elaborate placement of sponges in apertures to which an electrically conductive tab can contact even though that tab does not extend beneath the surface of the outer most layer. Representative examples of this construction is found in U.S. Pat. No. 4,522,211 (Bare et al.) and U.S. Pat. No. 4,838,273 (Cartmell).

Another biomedical electrode construction employs a reservoir of conductive gel into which a lead wire can be inserted through an aperture, as disclosed in U.S. Pat. No. 4,409,981 (Lundberg). Another biomedical electrode construction employs an aperture in communication with a conductive adhesive into which a lead wire can be inserted through the aperture, as disclosed in U.S. Pat. No. 4,715,382 (Strand).

SUMMARY OF THE INVENTION

The art needs a low profile multi-layer biomedical electrode that is simplistic in construction and easy to manufacture without losing the advantages of a tab-style biomedical electrode.

In one aspect, the invention provides a biomedical electrode that comprises:
 (a) an insulative backing having opposing major surfaces and an aperture extending between the major surfaces;
 (b) a field of ionically conductive medium contacting one major surface and extending into the aperture;
 (c) an electrically conductive tab disposed on the opposing major surface at least partially covering the aperture and having an electrically conductive surface contacting the field of ionically conductive medium at the aperture; and
 (d) a placement tape having an adhesive major surface covering at least a portion of the electrically conductive tab that covers the aperture.

A feature of the invention is the extremely low profile, multi-layer construction of the biomedical electrode in order to maximize flexibility and minimize discomfort during contact with mammalian skin.

Another feature of the invention is the ability to manufacture the multi-layer construction biomedical electrode by building layers of components of the electrode without requiring any one component to be placed in more than one layer of the multi-layer construction.

An advantage of the invention is the ease of manufacture and its consequential low cost for manufacture.

Embodiments of the invention are explained in relation to the drawings.

A BRIEF DESCRIPTION OF THE DRAWINGS

EMBODIMENTS OF THE INVENTION

Figure 1:
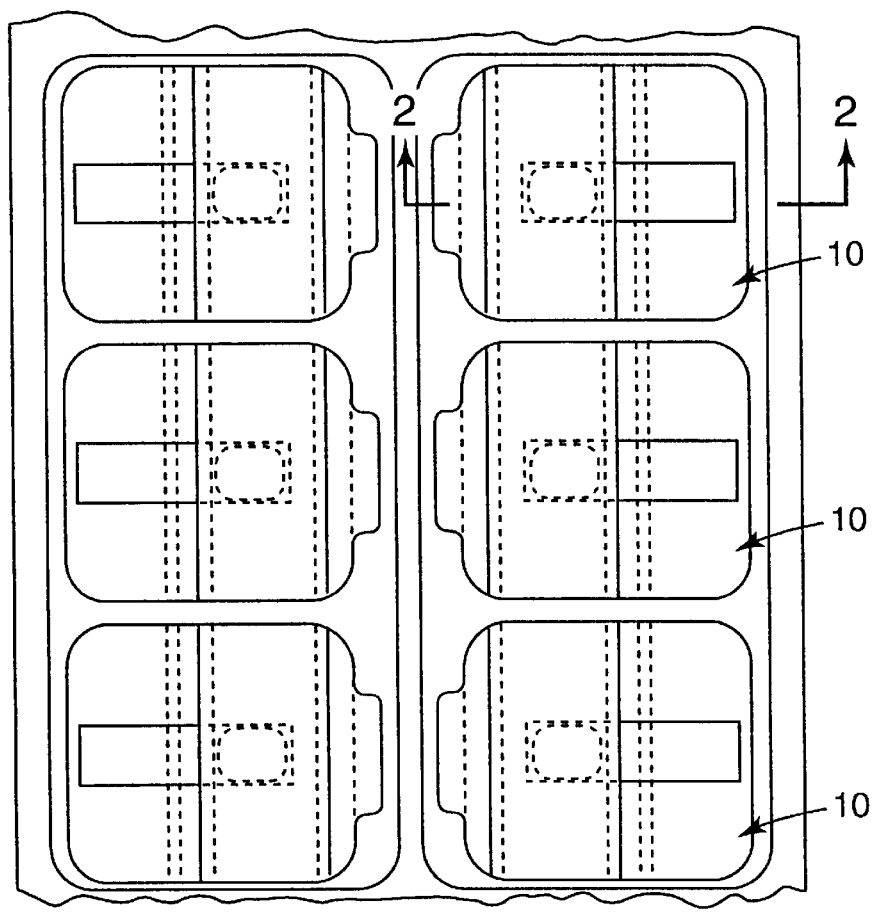
FIG. 1 is an embodiment of a biomedical electrode in an array with other biomedical electrodes after assembly.
Figure 2:
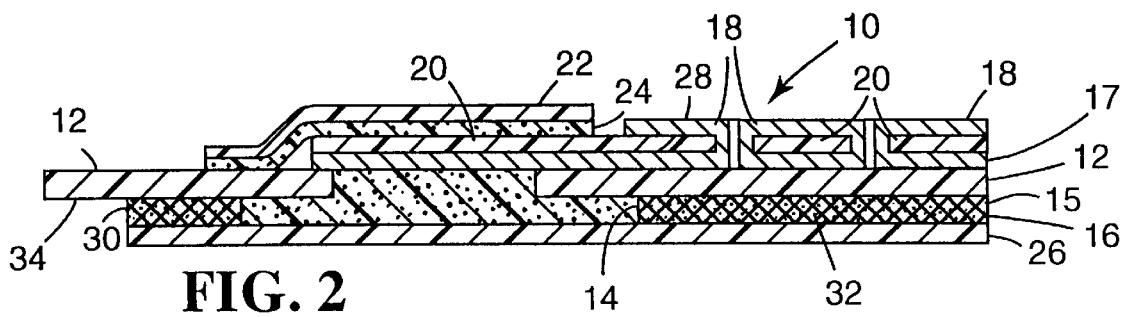
FIG. 2 is a cross-sectional view of a biomedical electrode of the present invention as seen in FIG. 1.

Referring to FIG. 1, an array of biomedical electrodes 10 are shown. Referring to FIG. 2, biomedical electrode 10 comprises a low profile, multi-layer construction comprising a backing 12 having an aperture 14 therein. On one major surface 15 of backing 12 is contacted a field 16 of ionically conductive medium, preferably a conductive pressure sensitive adhesive. Field 16 is constructed of an ionically conductive medium that can reside in the aperture 14 of backing 12.

Adjacent a second major surface 17 of backing 12 is an electrically conductive tab 18 having an electrically conductive surface 20 which is disposed on surface 17 at least partially covering the aperture 14. Electrically conductive surface 20 contacts field 16 of ionically conductive medium at the aperture 14.

Disposed over at least a portion of the electrically conductive tab 18 is a placement tape 22 having on a major surface a field 24 of placement adhesive. Placement tape 22 and field 24 adhere and restrain electrically conductive tab 18 at that portion of tab 18 covering aperture 14.

Protecting field 16 of ionically conductive medium is a release liner 26 until usage of electrode 10 is desired.

Optionally, a double-sided adhesive tape 28 can be used to assist in restraining a portion of tab 18 to surface 17 adjacent to aperture 14. The tape 28 places the terminus of tab 18 near, but not adhered to surface 17 of backing 12, to facilitate electrical connection to the terminus of tab 18.

Optionally, fields 30 and 32 of biocompatible pressure sensitive adhesive can be applied to surface 15 at locations distant from aperture 14 or completely cover surface 15 to assist in securing electrode 10 to skin and to minimize usage of more expensive ionically conductive medium used in field 16.

Optionally, a gripping tab 34 can extend from backing 12 for ease of removal of electrode 10 from liner 26 and for ease of removal of electrode 10 from skin.

Backing

Backing 12 is insulative, i.e., relatively electrically non-conducting. Backing 12 has an aperture 14 inside of its perimeter.

When an optional pressure sensitive adhesive is employed, then the perimeter of backing 12 contacts pressure sensitive adhesive extending beyond the perimeter of medium 16 such that a skirt of pressure sensitive adhesive 12 can be used to adhere electrode 10 to skin of patient. Optionally, a pressure sensitive adhesive layer can reside on at least a portion of major surface 15.

Nonlimiting examples of a suitable backing for use in the present invention are medical-grade pressure sensitive adhesive tapes such as those commercially available under the brands "Blenderm" or "Durapore" or a melt blown polyurethane material having a pressure sensitive adhesive coating on its major surface, such as that disclosed in U.S. Pat. No. 5,230,701 (Riedel).

Aperture 14 is constructed within the perimeter of backing 12 to permit contact between electrically conductive tab 18 and ionically conductive medium 16. Aperture 14 can be smaller or larger in any dimension within perimeter of backing 12 so long as there is sufficient area in aperture 14 to provide an interface at which electrically conductive tab 18 and its surface 20 can contact field 16 of ionically conductive medium.

Backing 12 has a thickness ranging from about 0.02 mm to about 0.89 mm and preferably 0.35 mm in order to provide a low profile layer of the multi-layer construction.

Ionically Conductive Medium

Field 16 of ionically conductive medium can be any ionically conductive electrolyte contacting major surface 15 of backing 12. It is an advantage of the invention for performance and manufacturing efficiency that field 16 contacts surface 15 as well as resides in aperture 14. Performance of the electrode 10 is enhanced by a larger area of field 16 contacting skin of a patient than the area required in aperture 14 for electrical communication with electrically conductive member 14. Less manufacturing registration is required with larger surface area for field 16.

Preferably, field 16 is an ionically conductive pressure sensitive adhesive that can adhere to major surface 15 and reside in aperture 14. If the medium is not inherently adhesive, then at least a portion of major surface 15 of backing 12 should be adhesive to retain a sponge or scrim into which the field of ionically conductive gel is impregnated, such that a portion of field 16 can form a sponge or scrim and enter aperture 14 for interface contact with tab 18. Nonlimiting examples of adhesive for major surface 15 include pressure sensitive adhesives, hot melt adhesives, and hot melt pressure sensitive adhesives.

Nonlimiting examples of ionically conductive media useful as field 16 in electrode 10 of the present invention include those ionically conductive compositions disclosed in U.S. Pat. Nos. 4,524,087 (Engel), 4,539,996 (Engel), 4,848, 353 (Engel); 4,846,185 (Carim); 5,225,473 (Duan); 5,276, 079 (Duan et al.); 5,338,490 (Dietz et al.); 5,362,420 (Itoh et al.); 5,385,679 (Uy et al.); copending, coassigned applications PCT Publication Nos. WO 95/20634 and WO 94/12585 and copending coassigned U.S. patent application Ser. Nos. US95/17079 (Attorney Docket No. 51537PCT4A), US95/16993 (Attorney Docket No. 51290PCT8A); and US95/16996 (Attorney Docket No. 48381PCT1A), the disclosures of which are incorporated by reference herein.

Thickness of the ionically conductive medium field 16 can range from about 0.25 mm to about 2.5 mm and preferably 0.63 mm in order to maintain a low profile, multi-layer biomedical electrode construction.

Electrically Conductive Tab

Electrically conductive tab 18 has an electrically conductive surface 20 which contacts field 16 of ionically conductive medium. When used for electrocardiography, electrically conductive surface 20 preferably is non-polarizable to enhance recovery of performance after defibrillation events. At least a portion of conductive tab 18 is placed over aperture 14 of backing 12 so that tab 18 can contact field 16 of ionically conductive medium in aperture 14. At least a portion of tab 18 can be contacted by a clamp or connector for electrical communication with electrical instrumentation, either to transmit energy into a body such as that used in transcutaneous electrical nerve stimulation or for receiving electrical signals from the body such as that used in electrocardiography.

Electrically conductive tab 18 can be a tab/pad construction comparable to that disclosed in U.S. Pat. Nos. 5,012,810 and 5,215,087, the disclosures of which are incorporated by reference. Tab 18 comprises an electrically nonconductive sheet of plastic coated with silver/silver chloride on surface 20 facing aperture 14 and field 16.

Alternatively, electrically conductive surface 20 can be constructed from materials disclosed in PCT Publications WO 94/26950 and WO 95/20350, the disclosures of which are incorporated herein by reference. Alternatively, surface 20 can be constructed from graphite materials disclosed in U.S. Pat. No. 5,215,087.

Optionally, surface 20 can reside on both major surfaces of electrically conductive tab 18. An advantage of multiple conductive surfaces 20 is the ease of electrical connection of electrode 10 to a biomedical connector regardless of the orientation of the connector to electrode 10 during connection. To permit both opposing major surfaces of tab 18 to be electrically conductive surfaces 20, tab 18 is perforated between its major surfaces to permit a coating forming surface 20 to cover surfaces lining such perforations to provide at least one electrical pathway between opposing major surfaces of tab 18.

Preferably, surface 20 is constructed of a silver/silver chloride ink commercially available as R301 MPK (+240) brand ink from Ercon, Inc. of Waltham, Mass.

Tab 18 preferably has a shape that it may either cover all of aperture 14 and is larger than aperture 14 with a portion extending beyond aperture 14 so that it can be connected to the electrical instrument. If tab 18 covers all of aperture 14, then a hot melt adhesive or a pressure sensitive adhesive can be applied as a skirt around aperture 14 to adhere tab 18 over aperture 14. Alternatively, tab 18 can be not as wide as aperture 14 and cover only a portion of aperture 14.

Figure 3:
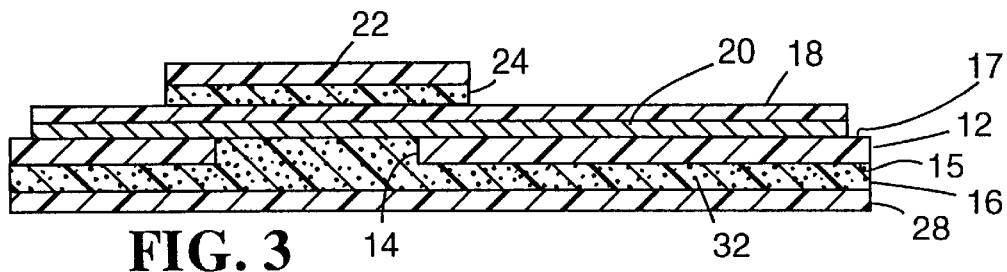
FIG. 3 is an alternate embodiment of the biomedical electrode, having opposing tab terminii.

In another embodiment seen in FIG. 3, tab 18 can extend from aperture 14 in different, preferably opposite, directions to provide at least two points of electrical contact to biomedical instrumentation. Preferably, tab 18 is positioned over aperture 14 such that nearly equal portions of tab 18 extend toward opposing edges of electrode 10 with tape 22 restraining tab 18 over aperture 14.

The thickness of tab 18 and surface 20 can range from about 0.025 mm to about 0.5 mm in order to maintain a low profile, multi-layer biomedical construction.

Placement Tape

Placement tape 22 having an adhesive field 24 on its major surface is one of several means for restraining at least a portion of electrically conductive tab 18 over that portion which covers aperture 14. Other means of securing tab 18 positioned over or in aperture 14 to contact field 16 of ionically conductive medium include mechanical anchoring such as staples, ultrasonic bonding, or variety of tapes having a variety of pressure sensitive, hot melt, or other adhesives or glues necessary to adhere tape 22 over tab 18. Another method of anchoring tab 18 to backing 12 is to have a pressure sensitive adhesive or hot melt adhesive field on surface 20 on areas not in contact with field 16, for example, around the aperture 14. Preferably, the adhesive field as a skirt around aperture 14 also provides a hermetical seal.

Preferably tape 22 is moisture impervious and has a pressure sensitive adhesive which can cover tab 18 and anchor it to the major surface 17 of backing 12. A moisture impervious tape 22 minimizes loss of moisture from ionically conductive medium that is exposed at the interface in aperture 14 and also prevents conductive tab 18 from separating from the remainder of electrode 10 when it is connected to an electronic instrument during usage. Further, tape 22 imparts to electrode 10 a distribution of mechanical forces from any wire connection between electrode 10 and electronic instrumentation. Preferably, tape 22 has elastic properties sufficient to resist delamination caused by mechanical forces of strain on wires connecting electrode 10 to instrumentation. Tape 22 can have dimensions that can control forces from tugging of a connector and lead wire to the biomedical electrode and also to provide conformance of the electrode to skin stretched beneath the electrode on the body of a patient.

Nonlimiting examples of placement tape suitable for those features described above include Scotch ™ Magic™ brand tape and Blenderm™ brand surgical tape, both commercially available from Minnesota Mining and Manufacturing Company. Optionally, such tape 22 can have trademark or other branding indica to identify the manufacturer of the electrode or provide other informational or regulatory markings for patient and practitioner usage. Tape 22 and adhesive field 24 can have a thickness ranging from about 0.03 mm to about 0.38 mm and preferably 0.2 mm in order to maintain a low profile, multi-layer construction for electrode 10.

Release liner

Release liner 28 can be any construction suitable for protecting the ionically conductive medium from contamination or loss of adhesion prior to usage. Commercially available release liners include "Polyslik" release liners commercially available from Rexam Release of Oakbrook, Ill.

Release liner 28 also provides a surface to prevent a dry out of ionically conductive medium field 16 when such medium is a polyelectrolyte.

Thickness of release liner 28 can range from about 0.03 mm to about 0.20 mm again to maintain a low profile, multi-layer biomedical electrode construction.

Optional Adhesiveness

Double-sided tape 28 can be any tape conventionally used to restrain a tab in a biomedical electrode construction.

Fields 30 and 32 of skin adhesive can be any conventional biocompatible pressure sensitive adhesive. Typically, acrylate ester adhesives will be preferred. Acrylate ester copolymer adhesives are particularly preferred. Such material are generally described in U.S. Pat. Nos. 2,973,826; Re 24,906; Re 33,353; 3,389,827; 4,112,213; 4,310,509; 4,323,557; 4,732,808; 4,917,928; 4,917,929; and European Pat. Publication 0 051 935.

In particular, an adhesive copolymer having from about 95 to about 97 weight percent iso-octyl acrylate and from about 5 to about 3 percent acrylamide and having an inherent viscosity of 1.1–1.25 dl/g is presently preferred.

Adhesive useful for double-sided tape 28 can be any of the acrylate ester adhesives described above used in double stick tape form. A presently preferred adhesive is the same adhesive as presently preferred for the skin adhesive except having an inherent viscosity of about 1.3–1.45 dl/g.

Method of Making Biomedical Electrode

Construction of electrode 10 is simplified over electrode constructions previously known in the art. One can begin with release liner 28 and form ionically conductive medium thereon, followed by placement of backing 12 with a prior punching of aperture 14 over the field 16 of ionically conductive medium. Thereafter, a registration placement of conductive tab 18 over aperture 14, followed by placement of tape 22 over tab 18 completes electrode construction from bottom to top.

When fields 30 and 32 are included in electrode 30, such fields 30 and 32 must be placed prior to placement of backing 12 using a pattern coating of adhesives such as that disclosed in copending, co-assigned U.S. patent application Ser. No. 08/343,253, the disclosure of which is incorporated by reference. When double-sided tape 28 is included in electrode 30, such tape 28 is placed on backing 12 before tab 18 is placed over aperture 14.

Equipment such as that shown in U.S. Pat. Nos. 4,795,516 and 4,798,642, which are incorporated by reference herein, disclose processes and equipment useful for dispensing strips of material from rolls and overlaying such strips in a registered, continuous manner in order to prepare electrode 10 of the present invention, either in the construction identified in FIG. 2 or in the construction identified in FIG. 1.

For an additional appreciation of the scope of the invention, the claims follow.

What is claimed is:

1. A biomedical electrode, comprising:
   (a) an insulative backing having opposing major surfaces and an aperture extending between the major surfaces;
   (b) a field of ionically conductive medium contacting one major surface and extending into the aperture;
   (c) an electrically conductive tab disposed on the opposing major surface at least partially covering the aperture and having an electrically nonconductive sheet of plastic coated with a first electrically conductive surface contacting the field of ionically conductive medium at the aperture and a second electrically conductive surface, wherein the tab has perforations between the first electrically conductive surface and the second elecrically conductive surface to permit a coating forming surface to cover surfaces lining the perforations to provide an electrical pathway between the first and the second electrically conductive surface; and
   (d) means for restraining at least a portion of the electrically conductive tab that covers the aperture.

2. The biomedical electrode, according to claim 1, wherein the electrode further comprises means for adhering the tab adjacent the aperture.

3. The biomedical electrode, according to claim 1, further comprising fields of biocompatible pressure sensitive adhesive at locations distant from the aperture.

4. The biomedical electrode, according to claim 1, wherein the ionically conductive medium comprises a sponge into which a field of ionically conductive gel is impregnated.

5. The biomedical electrode, according to claim 1, wherein the ionically conductive medium comprises an ionically conductive pressure sensitive adhesive.

6. The biomedical electrode, according to claim 1, wherein the electrically conductive tab extends in different directions to provide at least two points of electrical contact to biomedical instrumentation.

7. The biomedical electrode, according to claim 1, wherein the coating forming surface is constructed of an ink.

8. The biomedical electrode, according to claim 7, wherein the coating forming surface is a silver/silver chloride ink.

\* \* \* \* \*